United States Patent [19]

L'Esperance, Jr.

[11] Patent Number: 4,729,372

[45] Date of Patent: Mar. 8, 1988

[54] APPARATUS FOR PERFORMING OPHTHALMIC LASER SURGERY

[75] Inventor: Francis A. L'Esperance, Jr., Englewood, N.J.

[73] Assignee: LRI L.P., New York, N.Y.

[21] Appl. No.: 891,289

[22] Filed: Jul. 31, 1986

Related U.S. Application Data

[60] Continuation-in-part of Ser. No. 778,801, Sep. 23, 1985, abandoned, and a continuation-in-part of Ser. No. 742,225, Jun. 6, 1985, abandoned, and a continuation-in-part of Ser. No. 552,983, Nov. 17, 1983, abandoned, which is a division of Ser. No. 807,226, Dec. 10, 1985, abandoned, which is a division of Ser. No. 807,239, Dec. 10, 1985, abandoned.

[51] Int. Cl.$^4$ .............................................. A61N 5/06
[52] U.S. Cl. ................................ 128/303.1; 128/395; 350/6.2; 350/6.5; 350/315; 219/121 LG; 219/121 LP; 219/121 LQ
[58] Field of Search ................. 128/303.1, 362, 395; 350/6.2, 6.5, 6.9; 219/121 LA, 121 LG, 121 LW, 121 LZ

[56] References Cited

FOREIGN PATENT DOCUMENTS 1954802 10/1969 Fed. Rep. of Germany ...... 350/311
2257484 11/1972 Fed. Rep. of Germany ...... 350/311

OTHER PUBLICATIONS

"Excimer Laser Surgery of the Cornea", by Trokel et al., Am. J. Opthal, 93: 710-715, 1983.

Primary Examiner—Lee S. Cohen
Assistant Examiner—David Shay
Attorney, Agent, or Firm—Hopgood, Calimafde, Kalil, Blaustein & Judlowe

[57] ABSTRACT

The invention contemplates controlled ablation of the cornea, using ultraviolet laser radiation, wherein irradiated flux density and exposure time are so controlled as to achieve desired depth of the ablation. Sculpturing action results from controlled change of projected laser-spot size, in the course of a given treatment, wherein, in one illustrative case, projected laser-spot size ranges from a maximum which covers the entire area to be treated, down to a predetermined minimum tolerable size, wherein cornea-curvature change is myopia-corrective. Further illustrative techniques and situations are also disclosed, for achievement of hyperopia correction, for astigmatism correction, and in connection with corneal-transplant operations.

48 Claims, 33 Drawing Figures

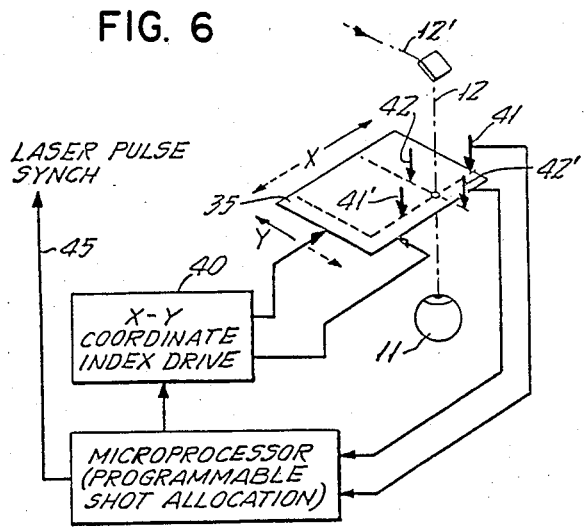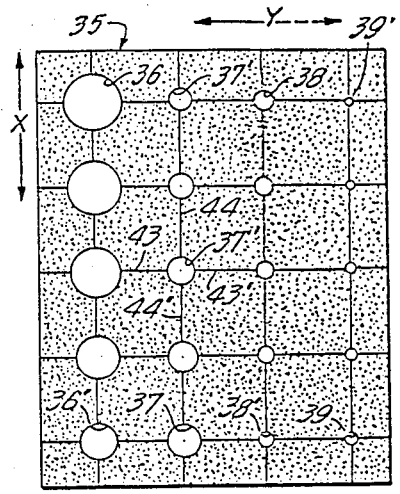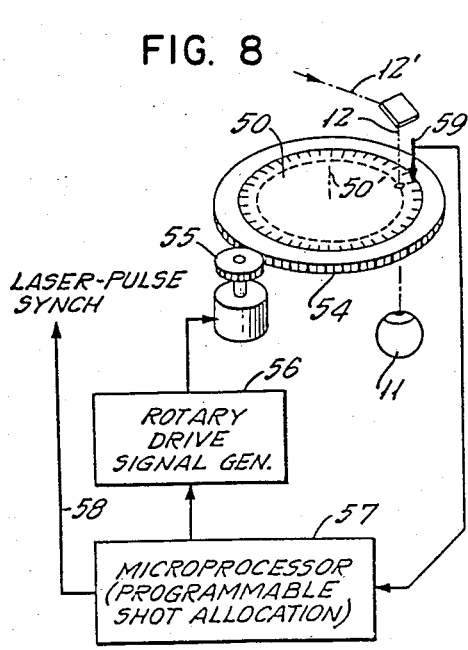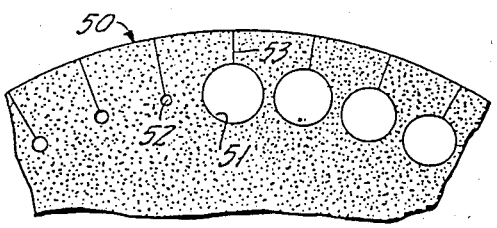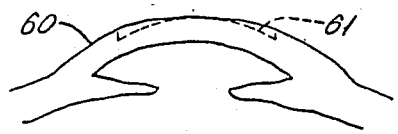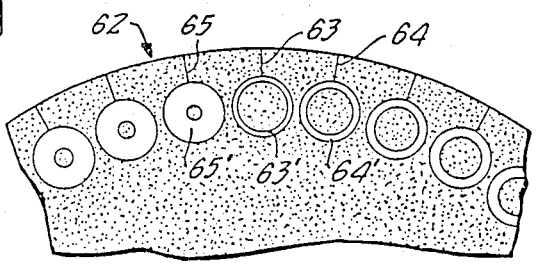

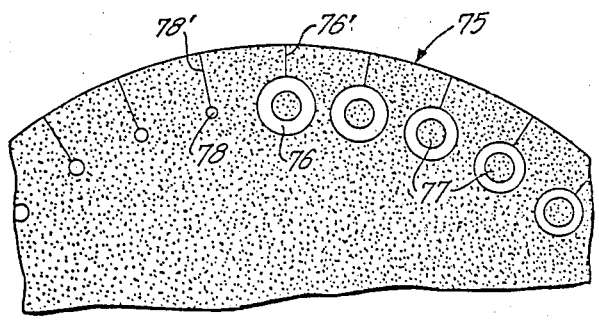
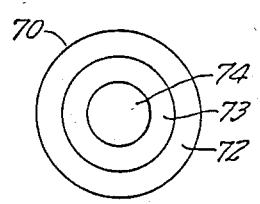
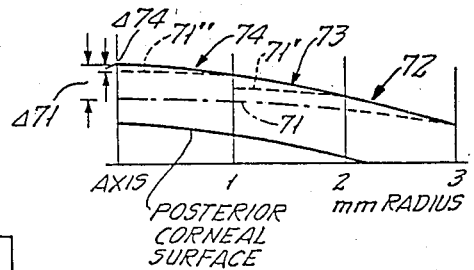
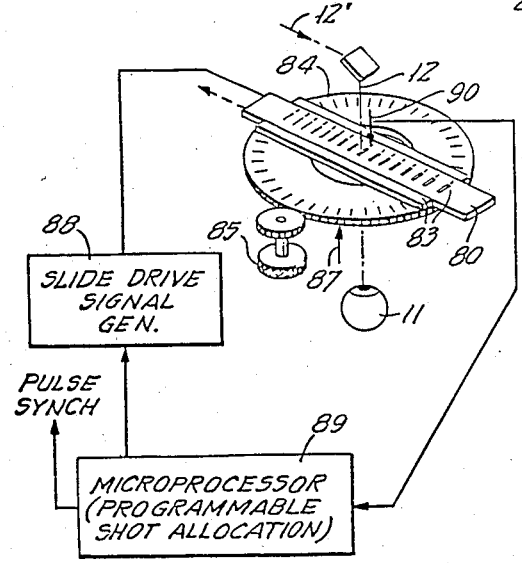
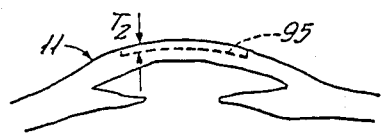
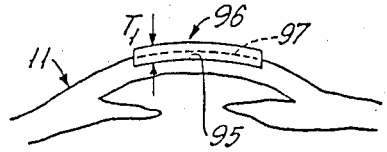
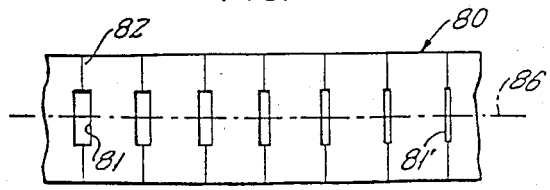

APPARATUS FOR PERFORMING OPHTHALMIC LASER SURGERY

RELATED CASE

This application is a continuation-in-part of copending application Ser. No. 778,801, filed Sept. 23, 1985, now abandoned and said copending application is a continuation-in-part of application Ser. No. 742,225, filed June 6, 1985 (now abandoned). Said application Ser. No. 742,225 is a continuation-in-part of my original application Ser. No. 552,983, filed Nov. 17, 1983 (now abandoned; and applications Ser. Nos. 807,226, filed Dec. 10, 1985 (now abandoned) and 807,239, filed Dec. 10, 1985 (now abandoned) are apparatus divisionals of said applications Ser. Nos. 742,225 and 778,801, respectively.

BACKGROUND OF THE INVENTION

The invention relates to that aspect of ophthalmological surgery which is concerned with operations upon the external surface of the cornea.

Operations of the character indicated include corneal transplants and keratotomies; such operations have traditionally required skilled manipulation of a cutting instrument. But, however keen the cutting edge, the mere entry of the edge into the surface of the cornea necessarily means a wedge-like lateral pressure against body cells displaced by the entry, on both sides of the entry. Such lateral pressure is damaging to several layers of cells on both sides of the entry, to the extent impairing the ability of the wound to heal, and resulting in the formation of scar tissue.

My original patent application Ser. No. 552,983, filed Nov. 17, 1983, includes a background discussion of the effects of various available wavelengths of laser radiation in ophthalmologic surgery and, in particular, surgery performed on the anterior surface of the cornea. It is explained that radiation at ultraviolet wavelengths is desirable by reason of its high photon energy. This energy is greatly effective on impact with tissue, in that molecules of tissue are decomposed on photon impact, resulting in tissue ablation by photodecomposition. Molecules at the irradiated surface are broken into smaller volatile fragments without heating the remaining substrate; the mechanism of the ablation is photochemical, i.e., the direct breaking of intra-molecular bonds. Photothermal and/or photocoagulation effects are neither characteristic nor observable in ablations at ultraviolet wavelengths, and cell damage adjacent the photodecomposed ablation is insignificant. The order of magnitude of this ablative process, in the case of radiation exposure at ultraviolet wavelengths (in the range of about 400 nm or less), is that an energy density of 1 joule/cm$^2$ incises to a depth of 1 micron ($1\mu$). Said original patent application discloses a technique of scanning a laser beam over the anterior surface of a cornea in such a controlled pattern as to sculpture said surface, imparting a new curvature to said surface, whereby to achieve optical correction of an optically deficient eye. But the scanner and scanner control to perform the technique are relatively complex and expensive.

BRIEF STATEMENT OF THE INVENTION

It is an object of the invention to provide an improved apparatus and technique for surgically operating upon the outer surface of the cornea.

Another object of the invention is to simplify and reduce the cost of apparatus and technique for surgically modifying optical properties of the eye through surgical procedure on the outer surface of the cornea.

It is a specific object to achieve the above objects with surgical techniques and apparatus for reducing a myopic, for reducing a hyperopic, and/or for reducing an astigmatic condition of an eye.

Another specific object is to provide an improved surgical technique in performing corneal-transplant operations.

A still further specific object is to achieve the above objects with automatic means for safely applying ultraviolet irradiation in surgical procedures on the cornea.

It is also an object to achieve the above objects without use of scanning techniques or apparatus.

The invention achieves these objects with apparatus which effectively fixes the position of an eye with respect to a non-scanning laser characterized by ultraviolet radiation, at an energy level capable of achieving controlled ablative photodecomposition of the cornea, namely, of the epithelium, Bowman's membrane, and stroma levels of the cornea. Irradiated flux density and exposure time are so controlled as to achieve desired depth of the ablation. As distinguished from the scanning procedure described in said application Ser. No. 552,983, a sculpturing action results from controlled change of projected laser-spot size, in the course of a given treatment, wherein spot size ranges from a maximum which covers the entire area to be treated for curvature correction, down to a predetermined minimum tolerable size. In one embodiment, a zoom lens in the optical path of projection is the means of changing spot size, and in another embodiment an indexible mask or mirror is employed; in both cases, the weighted allocation of time as function of spot size is such as to achieve a desired ultimate optically corrected cornea, from prior ascertainment of an optically deficient corneal curvature. Spot-size control is not only disclosed for effecting spherical-curvature correction, but also for cylindrical correction in reduction of astigmatism; still further use is described in connection with a corneal-transplant procedure.

DETAILED DESCRIPTION

The invention will be illustratively described in detail, in conjunction with the accompanying drawings, in which:

FIG. 6 is a simplified diagram schematically showing operative components of another embodiment of the invention;

FIG. 7 is a plan view of an indexible mask usable in the embodiment of FIG. 6;

FIG. 8 is a diagram similar to FIG. 6, to show a modification;

FIG. 9 is a fragmentary plan view of an indexible mask usable in the modification of FIG. 8;

FIGS. 10 and 11 are simplified diagrams to illustrate use of the invention, for the case of correcting a hyperopia condition;

FIGS. 12, 13 and 14 are simplified diagrams to illustrate use of the invention to achieve a Fresnel-type optically corrective contour at the anterior surface of the cornea;

Figure 19:
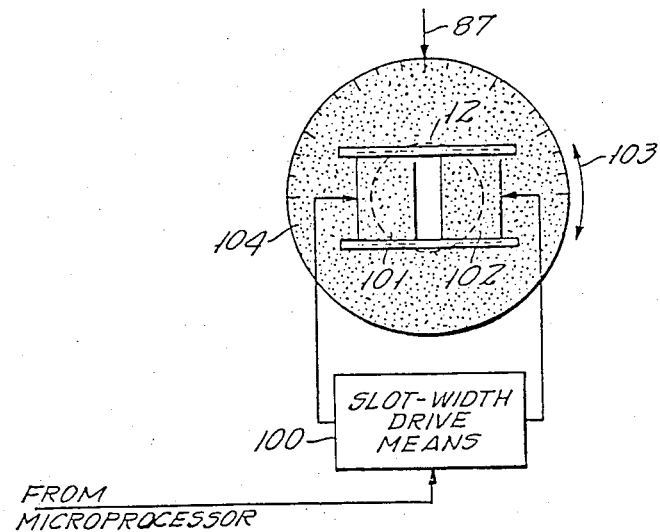
Figure 20:
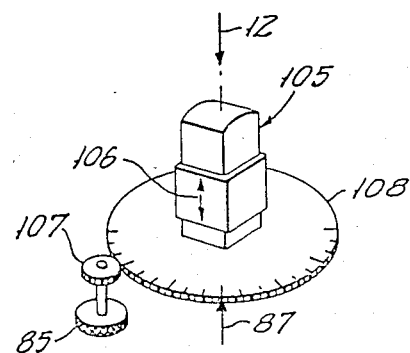
Figure 27:
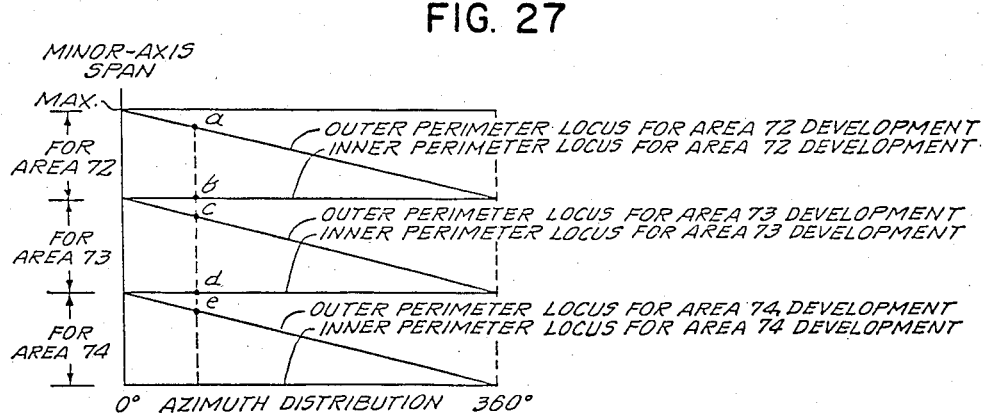
Figure 28:
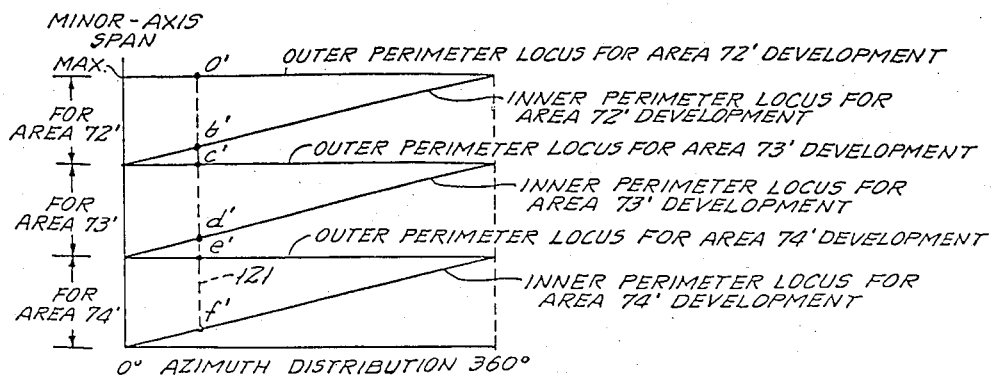
Figure 29:
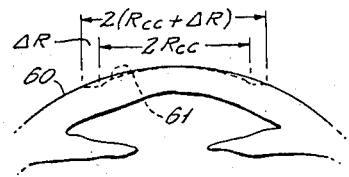
Figure 30:
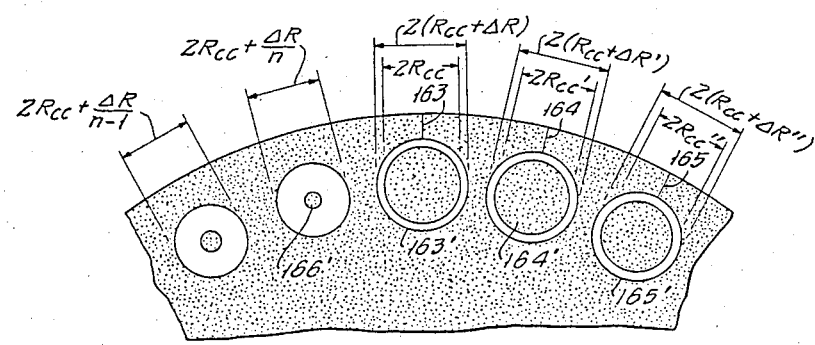
Figure 31:
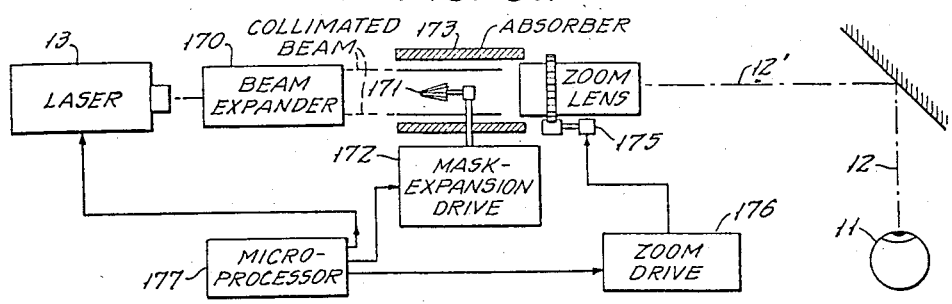

FIGS. 15 and 16 respectively illustrate components and features of an embodiment of the invention to achieve correction of an astigmatic eye;

FIGS. 17 and 18 are simplified diagrams to illustrate use of the invention in connection with a corneal-transplant operation;

FIGS. 19 and 20 are simplified diagrams to illustrate two different alternatives for the embodiment of FIGS. 15 and 16;

FIGS. 21 to 26 correspond to FIGS. 6, 7, 8, 9, 11 and 14, respectively, in illustration of a further aspect of the invention;

FIGS. 27 and 28 are graphical diagrams to illustrate a principle of reflector design;

FIGS. 29 and 30 are diagrams similar to FIGS. 10 and 11, respectively, to illustrate a special-purpose refinement of the invention;

FIG. 31 is a schematic diagram to illustrate an alternative for FIG. 30; and

Figure 32:
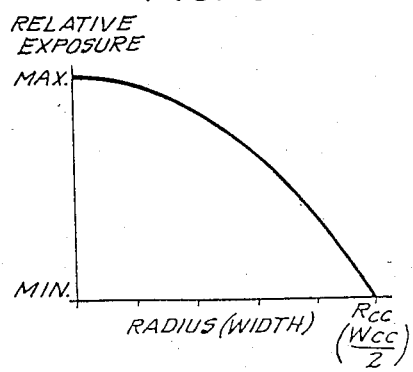
Figure 33:
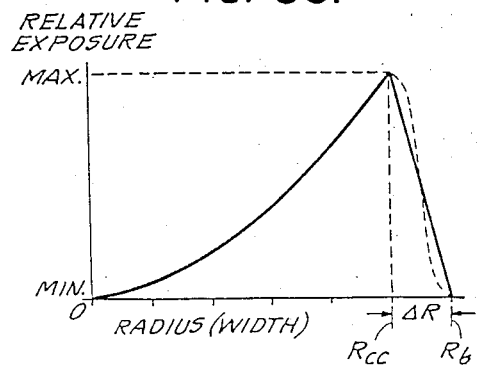

FIGS. 32 and 33 are similar diagrams illustrating different special-purpose refinements of the invention.

Figure 1:
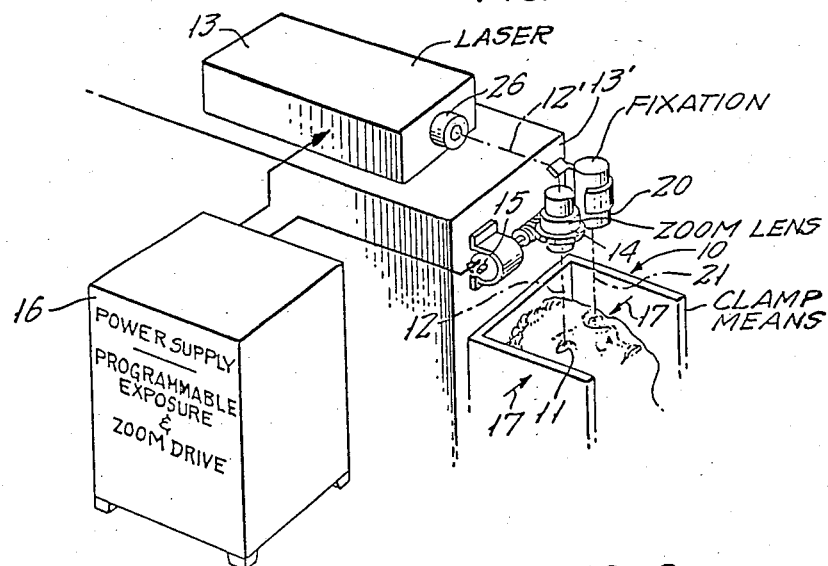
FIG. 1 is a schematic diagram in perspective, to show the general arrangement of operative components of the invention.

In FIG. 1, clamp means 10 is shown for fixed retention of the head of a patient (reclined, face up) such that the eye 11 to be operated upon is fixedly aligned with a downwardly folded portion 12 of the central axis 12' of beam output from a stationary laser device 13, supported by a table or other base 13'. The optical system of laser-beam projection to eye 11 includes zoom-lens means 14 having a reversible motor drive 15, whereby laser-spot size at eye 11 can be caused to vary from a predetermined minimum, to a maximum of 3 or 3.5-mm radius, corresponding to the corneal frontal area to be subjected to laser action. A cabinet 16 is shown by legend to include a power supply for the laser, and cabinet 16 is also shown (by legend) to include programmable microprocessor means for controlling exposure and beam (spot) size on axis 12, as will later become more clear.

Clamp means 10 preferably includes means, symbolized at 17, to stabilize the patient's head via opposed engagements at the region of his temples, and an eye-retaining fixture (18, in FIG. 2) peripherally engages eye 11 at the corneal-scleral area. Also preferably, an optical-fixation device 20 is adjustably fixed, as to the table or base 13'. Illustratively, device 20 includes a sighting reticle and lens, whereby the eye 11' not being operated upon can view the reticle as if at infinity; the sighting alignment 21 for device 20 is parallel to the axis 12, and it will be understood that adjustable means (not shown) may provide an adjustable offset, as needed for accommodation of the patient's inter-pupilary distance and to adapt to the particular mounted offset of device 20 from axis 12. For an operation on the other eye 11', the eye 11 will be available for similar fixation, in conjunction with another fixation device (not shown) and associated adjustably offsetting means; alternatively, the fixation device 30 may be adjustably mounted at correct offset on the opposite side of scanner 14. For purposes of operating on eye 11', clamp means 10 will have been indexed laterally with respect to laser 13 to the extent aligning axis 12 with the eye (11') then to be operated upon, thereby positioning eye 11 for use of the fixation device.

Figure 2:
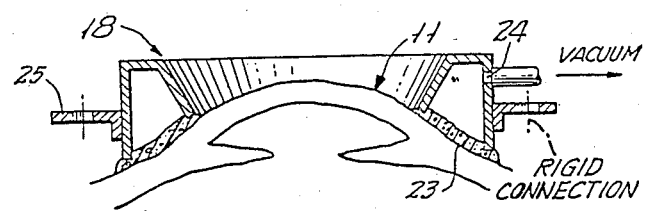
FIG. 2 is a simplified view in longitudinal section, showing an eye-retaining fixture used with the apparatus of FIG. 1.

The eye-retaining fixture 18 of FIG. 2 is seen to comprise a hollow annulus, having a convergent axial-end wall 23 of air-permeable material contoured to engage and retain the eye via a scleral-corneal region. A side-port connection 24 to a vacuum pump enables retention of eye engagement to wall 23, and outward lug or flange means 25 enables rigid aligned and spaced connection of fixture 18 to laser 13 and its scanner 14 via means suggested by legend in FIG. 2, such means being omitted from FIG. 1 for reasons of more simplified showing.

The laser selected for use at 13 preferably emits in the ultraviolet, namely, at wavelengths of less than substantially 400 nanometers. Such emissions for gas lasers are characteristically at 351-nm for xenon-fluoride lasers, 337-nm for nitrogen lasers, 308-nm for xenon-chloride lasers, 248-nm for krypton-fluoride lasers, 193-nm for argon-fluoride lasers, and 157-nm for fluorine lasers; and within this range, frequency-doubling techniques applied to other lasers, including crystal lasers, provide further alternative sources.

One of the existing commercial excimer-laser products of Lambda Physik GmbH, Gottingen, Germany, for example their Model EMG 103 operating with argon-fluoride, is satisfactory for use as laser 13; for this product, maximum energy per pulse is 200 milli-joules, with a pulse-repetition rate of 200 per second, $3 \times 10^5$ shots (pulses) being available from a single charge of the involved gas, before reducing to 50 percent of specified power at this repetition rate, it being noted that full rated power is not necessarily required in use of the present invention. Pulse width is about 15 nanoseconds, and typical beam dimensions are rectangular; as shown, however, the opening in a mask 26 reduces the laser beam to a circular section, and it will be understood that the optical elements of lens 14 are of quartz, calcium fluoride, magnesium fluoride, or otherwise as suitable for laser-beam accommodation.

Figure 3:
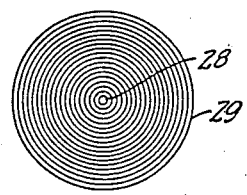
FIGS. 3, 4 and 5 are simplified diagrams to illustrate the nature of ablative corneal sculpture, performed with apparatus as in FIG. 1, for the case of correcting a myopia condition.

FIG. 3 is an attempt to depict the action of laser output as modified by the setting of zoom lens 14, it having already been indicated that, through the action of lens 14, spot size at eye 11 can be caused to vary from a minimum diameter at 28 to a maximum diameter at 29. The diagram shows a plurality of intermediate circular spot sizes, but it will be understood that since the zoom adjustment of lens 14 is continuously variable, there is no need to presuppose discrete circular spots of different diameter, except for the fact that in the course of a continuous variation in zoom adjustment the intermittent delivery of laser pulses will mean that each pulse is projected at a slightly different spot size.

Figure 4:
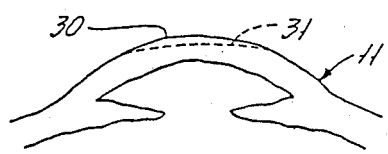
Figure 5:
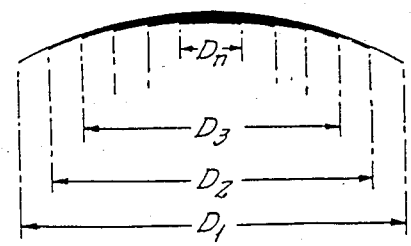

FIGS. 4 and 5 are illustrative of use of the invention in an optically corrective ablation of the anterior surface 30 of eye 11, wherein a myopia problem is to be solved, meaning that the curvature of surface 30 is of too-short radius to establish focus at the retina, for the case of distant objects. On the other hand, the dashed line 31 represents the ultimate curvature to which the anterior surface of the cornea should be modified to achieve a diopter-reducing corrective effect. To achieve the curve 31, the minimum desired photodecomposition is at the outer boundary 29, and the maximum is at the center. This is achievable by programming the microprocessor to progressively change the projected spot size (through driven adjustment of lens 14) in the course of a predetermined succession of laser pulses. The result is the same whether spot size is caused to expand from minimum (28) to maximum (29) or to reduce from maximum (29) to minimum (28). Of course, for each laser pulse or 'shot', ablative penetration into the cornea will be a function of delivered energy density, and therefore the number of pulses needed to achieve a given increment of ablative penetration will be greater, the larger the diameter of the projected spot.

FIG. 5 is a very much simplified diagram to represent the progressive ablative effect of a succession of laser-spot projections at successively reducing diameters $D_1$, $D_2$, $D_3$ ... $D_n$. The least resulting energy density is at the largest diameter $D_1$, which can be assumed to have made the least penetration, although such penetration will have been uniform over the entire spot area for diameter $D_1$. An incrementally greater energy density results at the next step $D_2$ of diameter reduction, in which event penetration has become cumulative with that of the first shot, over the area common to both shots. The cumulative penetration effect continues for shots of successively reduced diameter, so that a new, larger-radius curvature emerges from a pattern of stepped reduction in projected spot size. However, for a sufficiently great number of laser pulses (and hence, potentially discrete steps), individual steps cease to appear discrete, and a sufficiently smooth new spherical anterior surface characterizes the cornea. This is particularly so after a post-operative period of about two days, by which time a thin epithelial layer will have spread into smooth and protective coverage of the newly characterized surface.

The foregoing discussion in connection with FIGS. 1 to 5 presupposes a pulsed laser, exemplified by an excimer laser. But other lasers are known to emit at presently suitable energy levels and at ultraviolet wavelengths of present utility, and these other lasers will emit continuously for periods of controlled duration. For example, an organic-dye laser utilizing the proper organic dye can be made to produce laser emission in the region of 380-nm when pumped by ultraviolet laser sources such as a continuous-wave frequency-quadrupled neodymium-YAG laser operating at 266-nm; in this case, the organic-dye laser emission at 380-nm can be frequency-doubled by a proper non-linear crystal such as a potassium-deuterium-phosphate (KDP) crystal or a potassium-titanium-phosphate (KTP) crystal to an emission wavelength at 190-nm. The showing of FIGS. 1 to 5 will thus be understood to illustrate the further case wherein ultraviolet laser radiation on axis 12 is of continuous-wave nature, for a treatment duration predetermined by programming at 16, and wherein the programming at 16 further continuously drives the zoom-lens 14 to provide that time-variation of projected spot size as has been predetermined to achieve a myopia-correcting change in curvature, from curve 30 to curve 31, in the course of the treatment duration. And this result is achieved whether spot size (at the eye 11) is caused to expand continuously from minimum (28) to maximum (29) or to reduce continuously from maximum (29) to minimum (28).

In the embodiment of FIGS. 6 and 7, a masking technique is employed, in place of the zoom-lens technique of FIG. 1, to achieve a similar myopia-correcting curvature change in the anterior surface of the cornea. Such masking could proceed continuously with a suitably programmed variable iris diaphragm in place of lens 14, but in the form shown, a single precision masking plate 35 is employed. The masking plate 35 is rectangular and is mounted (by means not shown) for indexed unit displacement in each or both of two orthogonal axes X–Y. For each of the grid-like layouts of mask openings provided on plate 35, the size of the involved circular opening incrementally changes. Thus, for a first row of mask openings beginning and ending with openings 36 and 36', respectively, the openings are of progressively reducing diameter; in the next-adjacent row, beginning and ending with openings 37 and 37', respectively, the openings continue with progressively reducing diameter; in the third row, the progression continues to reduce from opening 38 to opening 38', and the final row reduces still further from 39 to the smallest opening 39'. An X-Y coordinate index drive 40 will be understood to provide correct X and/or Y successive displacements of masking plate 35 under control of microprocessor means 41 having programmable means for allocating numbers of excimer-laser 'shots' (or, in the case of a CW laser, for allocating variously controlled pulse duration) at particular succeeding mask-opening sizes, whereby to effect a given desired ablative "sculpture" which will predictably and correctively change optical performance of the eye (11). As shown, optical-transducer elements in pairs 41–41' and 42–42' straddle each mask opening as it is indexed into the laser-projection axis 12; these transducer elements sense registry with grid lines, such as x-positioning grid lines 43–43' on opposite sides of a given mask opening 37" (FIG. 7) and orthogonally related y-positioning grid lines 44–44' on opposite sides of the same mask opening 37", whereby such registry may be certified to the microprocessor 41, for interlock purposes, to achieve correct mask-opening positioning on axis 12 before firing the next laser pulse, the latter being symbolized by a synchronizing connection 45.

In the arrangement of FIGS. 8 and 9, myopia-correcting sculpture relies on indexed shifting from one to another of successive different-area mask openings, via incremental angular indexing displacement of a masking disc 50 (about an indexing axis 50'); disc 50 has a peripherally distributed succession of mask openings, ranging from the largest opening 51 to the smallest opening 52. A radial mark, as at 53 for opening 51, identifies the angle at which the given opening is correctly indexed into position on the laser-projection axis 12. Disc 50 is shown mounted to an annular ring 54 which will be understood to be counterbored for central and keyed location of disc 50, and ring 54 is edge-driven by suitable means 55 under control of a rotary-drive signal generator 56. Again, a programmable microprocessor 57 is responsible for controlling the rotary-index drive 55–56 for predetermined allocation of laser pulses to given mask openings, to achieve the desired cornea-profile correction, with laser-pulse synchronization via lines 58, as an optical transducer 59 tracks registry with the particular radial-marker line for each given mask-opening area.

FIGS. 10 and 11 illustrate that the device of FIG. 8 is equally adaptable to making corrective sculpture of the cornea 60 of a far-sighted (hyperopic) eye, meaning that the anterior curvature is to be increased, as to achieve a new profile 61 (FIG. 10). This is illustratively done by substituting a different masking disc 62 for the disc 50 of FIG. 8. In the disc 62, for each of the angular mark locations (as at 63), a basic opening limit, e.g., of 3.5-mm radius, is the outer edge of each of an angularly distributed succession of annulus openings, produced by a central opaque masking spot of progressively changing diameter. Thus, for the smallest annular mask area 63'

(which applies at radial mark 63), the central opaque spot is a circle of nearly the diameter of the basic limiting opening, to produce a first, or thinnest annulus 63'. At the next mark 64, the outer diameter of a slightly thicker annulus 64' is determined by a central opaque spot of slightly lesser area. The progression continues, at increments of equal angle (about the index axis of disc 62), until reaching the largest annular opening 65' at angular location 65, where the central opaque masking circle is of least diameter. In use of the mask 62 in conjunction with the positioning and control apparatus of FIG. 8, the microprocessor 57 will be understood to so allocate laser pulses to particular sizes of annular mask openings that greatest cumulative ablative penetration of the cornea is at larger radii, while least penetration is at smaller radii, resulting in the corrected ultimate profile 61 of decreased radius.

The arrangement of FIGS. 12, 13 and 14 illustrates that above-discussed principles of the invention are further applicable to corrective sculpture of the cornea to achieve a Fresnel-type distribution of the desired ultimate curvature, which can be either hyperopia-correcting or, as shown, myopia-correcting. Such an operation (i.e., Fresnel-type) would be used when, in the surgeon's considered judgment, a single smoothly developed corrected curvature would entail excessive removal of tissue at the involved region of necessarily deepest cut. To avoid too deep a cut, FIGS. 12 and 13 illustrate that an ultimately reduced-curvature surface, as at 31 in FIG. 4 (dashed line 71 in FIG. 13), is achieved in annular increments within the field bounded at 70. In the outer one of these annuli (72), the curvature and depth of cut are precisely as would have applied to generate the continuous curve 71 (i.e., without Fresnel steps). But the intermediate annular area 73 effectively achieves a continuation of curve 71 with much less volume of corneal excision. Finally, the inner circular area 74 effectively completes curve 71, with minimal removal of corneal tissue.

The removal of tissue at the center is denoted $\Delta 74$ for the Fresnel cut 74 of FIGS. 12 and 13 and, comparatively, is but a small fraction of the maximum removal depth $\Delta 71$ which would have been needed to achieve the same optical correction with the smoothly developed corrected single-curvature surface 71. FIG. 14 illustrates an indexible rotary masking disc 75 of a type compatible with the system of FIG. 8, in substitution for the disc 50 of FIG. 8, to achieve Fresnel-type cuts of the nature described for different annuli 72, 73, 74. Beginning with the largest area of mask annulus 76 (at location 76') and proceeding for a first 120° sector of disc 75, the succession of annular mask openings will be understood to progress with decreasing radius, by reason of a constant-area central mask spot, in the context of a progressively shrinking outer-circle diameter. The programmable means 57 (of FIG. 8) will be understood to function as a control for allocation of laser-pulse shots, using a programmed distribution of the annular mask openings of this first sector, for achievement of the curvature 71 within outer annulus 72. A similar succession of annular mask openings will be understood to be similarly accessible via a second sector (not shown) of mask disc 75, in establishing the curvature 71' within the intermediate annulus 73. And finally, the curvature 71" is established within the inner circular area 74 by programmed projection of laser shots on axis 12, through an indexibly available succession of progressively shrinking circular openings, beginning with a mask-opening diameter of largest (circle-74) area, and reducing throughout the third sector to the smallest opening 78 at location 78', adjacent the location 76' (of the first sector).

The diagrams of FIGS. 15 and 16 are illustrative of the variable aperture or indexible-mask technique of the invention in the development of corrections for astigmatism, by ablative laser pulsing with a rectangular beam section wherein the width of the section is changed to create a cylindrical profile of cumulative ablative penetration. This can be done by masking the laser beam with a slit or diaphragm of variable width, and with the ability to selectively rotate the orientation at which the major dimension of the slit is positioned (i.e., based on prior measurement of the angle and of the cylindrical diopter strength of the particular eye's astigmatism; however, in the form shown in FIG. 15, the mask is an elongate strip 80 having a succession of rectangular slit openings of progressively different width. In the fragmentary showing of FIG. 16, these openings proceed from a largest area opening 81 to a smallest area opening 81', and the central axis of symmetry of each of these openings is identified with a mark, as at 82 for opening 81; preferably, all such marks are at equal spacing.

Strip 80 is a slide guided by means 83 forming part of a rotatable mask-supporting disc or ring 84; and guide means 83 locates the longitudinal axis 86 of slot symmetry on a diameter of ring 84. Manually operable means 85 has edge-drive coupling to ring 84 to enable selective angular orientation of strip 80 (about the laser-projection axis 12), as by observation via a fixed indicator mark 87 against azimuth edge markings on ring 84. A bidirectional slide-drive signal generator 88 is under control of a microprocessor 89 to coordinate slide (80) positioning with laser-pulse control, suitably synchronized by optical-transducer (90) tracking of the mark (82) applicable to the particular indexed mask opening, whereby each mask opening can be assuredly on the axis 12 of laser-beam projection.

In use of the invention for laser surgery upon an eye having need for both astigmatic and spherical correction, it is preferred that the astimatic correction, described in connection with FIGS. 15 and 16, be the first of two procedures. This is considered advantageous because astigmatic errors are generally not as severe as spherical errors, so that fewer diopters of cylindrical curvature ablation will be involved than for the subsequent spherical-correction procedure. Furthermore, to have eliminated or substantially eliminated the astigmatism in a first procedure is to have constituted the anterior surface of the cornea to an essentially spherical surface, which (be it myopic or hyperopic in nature) is more assuredly correctively sculpted to the desired profile (also spherical) for emmetropia vision, particularly where, as in the case of this invention, all ablative-laser shots (whatever the currently operative mask opening) are effectively centered on the optical axis of the involved eye.

Quite aside from the variable-depth character of the removal of corneal tissue (FIGS. 4 and 10), the invention also lends itself to uniform-depth removals, over a single entire area of the cornea, in preparation for reception of a corneal transplant. In FIGS. 17 and 18, the cornea of an eye 11 is subjected to a succession of laser pulses which have been masked to the same area, of diameter D, e.g., 7-mm; the succession of pulsed laser shots will in such case be seen to produce a carved base or recessed-floor curvature 95 for reception and location of an implanted corneal transplant. Alternatively, in FIGS. 17 and 18, the cornea of eye 11 may be subjected to steady (CW) laser exposure of such intensity as to ablate (a) via the same mask on constant diameter D and (b) at a rate of ablative penetration for which a given duration (exposure time) of laser-beam projection will achieve the desired depth of penetration.

Further with respect to a corneal-transplant procedure, the described apparatus will be seen to be further useful, as in preparation of the corneal insert to be implanted at and within the recess 95. A donated eye may be reversibly held to a fixture as described at 18 in FIG. 2; by 'reversible' it is meant that, depending upon the manner of mounting flange 25, either the epithelium or the endothelium of the donated eye may be mounted for upward exposure to the laser beam 12, it being understood that for the latter situation with the donated eye, iris and other regions not needed for corneal-scleral mounting and for corneal operation will have been initially removed. A preferred procedure is first to so expose to laser action the concave inner side of the donated cornea; such action is to an extent (achieved by timed CW exposure, or by multiple pulsed-laser shots, of a full circular field exceeding the diameter of recess 95) sufficient to remove tissue at least to a uniform depth within the donated stroma, whereupon the mounting of fixture 18 (and its partially machined corneal workpiece) is reversed, to expose to laser action the convex outer side of the donated cornea. Laser action on the outer side consists of two steps: first, timed CW exposure multiple laser pulses of the full circular field (exceeding the diameter of recess 95) thereby excising at least the epithelium and to a depth which preferably achieves a transplant thickness $T_1$ exceeding the depth $T_2$ of recess 95; second a scanner (not shown, but of the type disclosed in my said pending patent application, Ser. No. 552,983) is operated in a line-cutting mode wherein successive laser pulses sequentially advance along the circumference of a circle designed for precise acceptance in the circular recess 95, until full severance of the circular cut-out, which then becomes the prepared transplant. Upon implanting, donated stroma is placed in full endothelium-free contact with the patient's prepared stroma, and the implant may be sutured. Later, upon removal of sutures, the outer surface of the eye 11 and its transplant 96 will have the appearance shown in FIG. 18, wherein the transplant projects beyond adjacent areas of the patient's cornea, and this projecting surface of the transplant may be reduced by above-described laser sculpting to a finish contour 97 of preferably flush marginal conformance with non-sculptured adjacent tissue of the patient's eye. It will be further understood that, subject to the surgeon's decision, such a finishing cut may be to a curvature which does or does not effect a predetermined change in optical performance of the eye.

It will be seen that the described methods and apparatus achieve all stated objects and provide readily controlled procedure for correcting eye abnormalities attributable to cornea curvature. The ablative penetration of laser-beam action may be kept to a relatively harmless fraction of the thickness of the cornea, and whatever the depth of invasion, a natural body process provides protective epithelium coverage of the sculpted region, within a few days after an operation. The programmable coordination of laser-beam size and shape (circular, annular, or rectangular) in conjunction with numbers of pulses at given sizes and shapes will produce predictable and controlled changes in curvature, whereby cylindrical errors and/or spherical errors may be eliminated or substantially reduced, to the enhanced comfort and convenience of the patient.

While the invention has been described in detail for various illustrative embodiments and modes, it will be understood that modifications may be made without departing from the spirit and scope of the invention. For example, what has been described above as manual means 85 to present the angle at which astigmatic correction is to be achieved, may in fact be an automatically driven setting of the astigmatic-correction angle, wherein the angle-input data for making the automatic drive is produced by a diagnostic system or method as described in my copending patent application, Ser. No. 691,923, filed Jan. 16, 1985.

Also, by way of example, achievement of cylindrical sculpting in reduction of astigmatism does not necessarily require the indexible-slot technique of FIGS. 15 and 16. As a first alternative (FIG. 19), the variation in slot width may be achieved electro-mechanically, via microprocessor control of means 100 to differentially drive opposite side plates 101–102 of a variable-width opening which is always centered on the axis of the projected laser beam 12, plates 101–102 being slidably mounted to an annular base 104 which is adjustable in rotation to the angle for which astigmatism is to be reduced (as suggested by a double arrow 103). As a second alternative (FIG. 20), a cylindrical-lens zoom system 105 is motor-driven by microprocessor output (as suggested by double arrow 106) to establish a shaping of the projected laser beam 12 to a line of variable width, and said line is settable to the angle for which astigmatism is to be reduced, as by edge-drive means 107 to the rim 108 of an annular mount for zoom system 105.

FIGS. 21 to 26 are illustrative of a different aspect of the invention wherein the variously described sequences of spot shaping to achieve laser-ablated corneal-curvature change are produced by reflection techniques. And because the identification of parts in these figures corresponds with parts in FIGS. 6, 7, 8, 9, 11 and 14, the same numbers are used, as applicable, in a 100-series.

Figure 21:
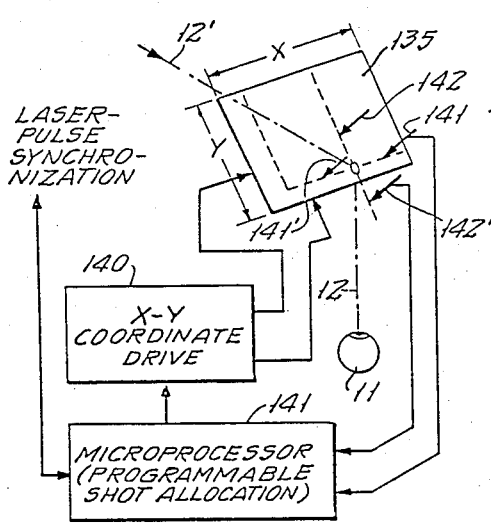
Figure 22:
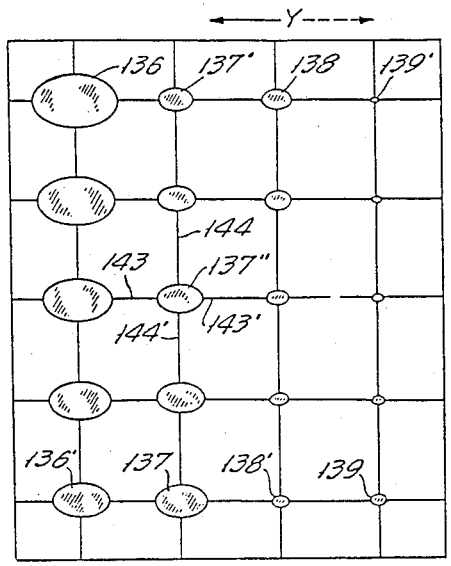

In the embodiment of FIGS. 21 and 22, a transparent plate 135, as of quartz, is characterized by a succession of elliptical reflection areas, oriented with their major axes parallel and respectively centered on each of the two-dimensionally (X-Y) indexible positions of plate 135. For each of the grid-like layouts of elliptical reflecting areas on plate 135, the size of the involved ellipse incrementally changes. Thus, for a first row of reflective ellipses beginning and ending with areas 136 and 136', respectively, the areas are progressively reducing; in the next-adjacent row, beginning and ending with areas 137 and 137', respectively, the reflecting ellipses continue their progressive reduction; in the third row, the progression continues to reduce from area 138 to area 138'; and the final row reduces still further from 139 to the smallest, 139'. Support for indexing displacement of plate 135 will be understood to position the reflective side thereof in inclined facing relation to the laser-output beam alignment 12', the inclination being preferably such that the major axis of each of the ellipses is at 45° to alignment 12' when the center of the particular ellipse has been indexed for intersection with the alignment 12'; at the same time, the minor axis of each ellipse is at 90° to alignment 12' when the center of the particular ellipse has been indexed for intersection with alignment 12′, and the major/minor axis-span relation is $\sqrt{2}:1$. This preferred relation determines that for each ellipse-index position, the reflection 12 of the laser beam will be at 90° to the alignment 12′ and that this reflection will be a circle of diameter equal to the minor-axis span of the involved ellipse. The X-Y coordinate index drive 140 and the microprocessor 141 perform as described for FIGS. 6 and 7, and optically readable grid lines on plate 135 (between the reflective ellipses) enable optical-transducer pairs 141-141′ and 142-142′ to assure precise positioning of each reflecting ellipse, centered on axis 12′, before firing the next laser pulse.

The automated running of the FIG. 21 device, in the full two-coordinate program of indexing plate 135, will be seen to deliver the greatest density of ablating energy in the central part of the total circular corneal area which is operated upon, with such density decreasing as a function of increasing radius from the optical axis of the eye. The curvature change is therefore of myopia-correcting nature.

Figure 24:
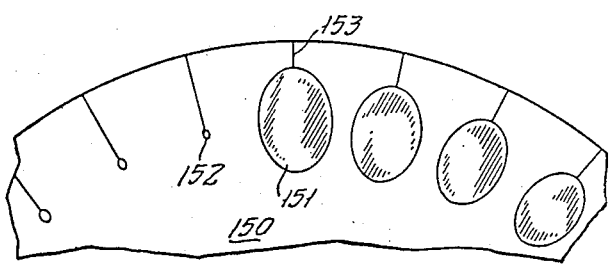
Figure 23:
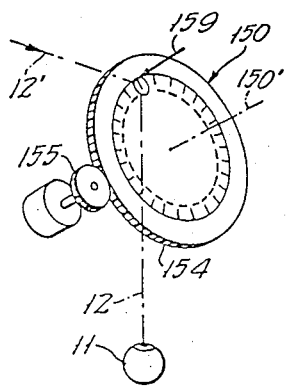

The embodiment of FIGS. 23 and 24 has its correspondence to FIGS. 8 and 9, and thus the circumferentially distributed pattern of reflecting ellipses is on an indexible circular plate or disc 150, plate 150 being suitably transparent and of quartz. Preferably, the centers of all ellipses are on one geometrical circle about the index axis 150′, and the index axis 150′ is oriented to bisect the right-angle relation between laser axis 12′ and the (reflected) projection axis 12 to the eye, axis 12 being aligned with the optical axis of the eye 11; also preferably, the major axis of each of the ellipses is oriented radially of the indexing center of plate 150, and, again, the major/minor axis relation of all ellipses is $\sqrt{2}:1$. The automated running of the rotary-indexed FIG. 23/24 arrangement will be seen to produce the same cornea-ablating result as the orthogonally indexed FIG. 21/22 arrangement, so that the result is again myopia-correcting.

Figure 25:
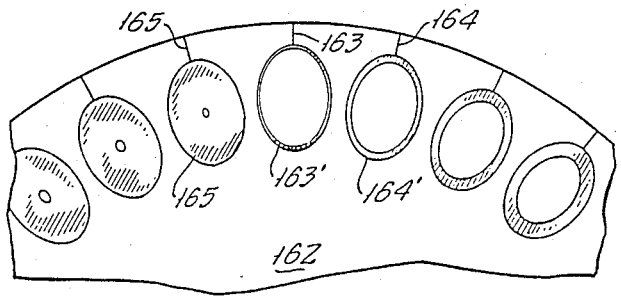

The fragmentary showing of FIG. 25 illustrates that upon substitution of a different circular reflecting plate 162 (in place of plate 150 of FIG. 24), the microprocessor programming of rotary indexing and of laser pulsing will produce a hyperopia-correcting change in cornea curvature, of the nature shown in FIG. 10. The reflecting ellipses of FIG. 25 are in an angularly spaced succession of elliptical annuli of constant outer periphery; the succession ranges from the radially thinnest ellipse 163′ at index location 163, to the radially thickest ellipse 165′ at index location 165. in other words, the succession of reflecting ellipses of FIG. 25 accounts for annular projection of a constant outer diameter and of a varying inner diameter, throughout a single indexed rotation of plate 162, accounting for maximum ablating penetration of the cornea at the outer diameter, and progressively reduced ablating penetration as a function of decreasing radius about the optical axis of eye 11. For all ellipses, the major/minor axis ratio is $\sqrt{2}:1$, in view of the 45° incidence of the laser beam on each indexed elliptical reflector.

Figure 26:
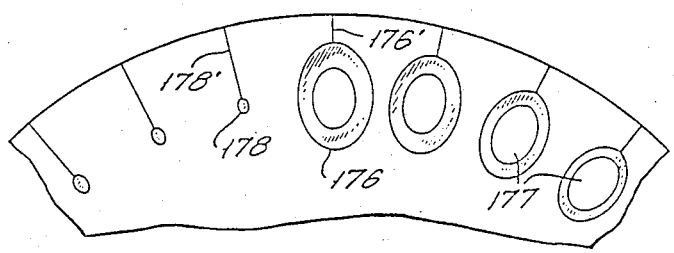

The arrangement of FIG. 26, taken with FIGS. 12 and 13 is illustrative of the application of the reflection principles of FIGS. 24 and 25 to corrective sculpture of the cornea to achieve a Fresnel-type distribution of the desired ultimate curvature, which, as for FIG. 15, can be either hyperopia-correcting or, as shown, myopia-correcting. To avoid too deep a cut of ablative penetration, the ultimate reduced-curvature surface, as at 31 in FIG. 4 (dashed line 71 in FIG. 13), is achieved in annular increments within the circular area bounded at 70, and the curvature 71 is produced at steps 72-73-74.

As shown in FIG. 26, a transparent plate 175 serves as a replacement for plate 150 in FIG. 23 and is provided with an angularly stepped progression of reflecting elliptical annuli, beginning with the largest and thickest elliptical annulus 176 at location 176′, and proceeding clockwise to the next elliptical annulus of incrementally smaller size and thickness, based on an inner limiting ellipse 177 of constant size. For the three-step profile 72′73′74 shown, the reflecting elliptical annuli based on the same inner limiting ellipse 177, are distributed over a first 120° sector of disc 175, with the outer elliptical periphery progressively shrinking to a final radially thin ellipse (not shown); and the programmable means 57 (of FIG. 8) will be understood to function as a control for allocation of laser-pulse shots, using a programmed distribution of the first-sector elliptical reflectors, for ablative achievement of the curvature 71 within outer annulus 72. A similar succession of reflecting elliptical annuli will be understood to be similarly indexible over a second 120° sector (not shown) of disc 175, in establishing the curvature 71′ within the intermediate annulus 73. And finally, the curvature 71″ is established within the inner circular area 74 by programmed projection of laser shots on axis 12′, through an indexibly available succession of progressively shrinking elliptical areas, beginning with an ellipse of largest minor-axis span (not shown, but equal to the diameter of the central circular area 74), and reducing throughout the third 120° sector to the smallest reflecting ellipse 178 at location 178′, adjacent location 176′ of the first sector.

A full rotation of disc 175, in the context of suitably programmed pulsed-laser delivery on alignment 12′, thus creates the Fresnel steps 72-73-74 in succession. But it will be understood that by using the highly precise photo-reduction and metal-disposition techniques available from micro-circuit technology, each indexed step of a single disc (not shown) may be instrumental in the progressive formation of all annular components of a full Fresnel-type ablation pattern. To create reflecting elliptical patterns to achieve this result, FIG. 27 outlines the course of minor-axis size variation for all involved reflecting ellipses, for the case of myopia-correction, and FIG. 28 similarly outlines the course of minor-axis size variation for all involved reflecting ellipses, for the case of hyperopia correction.

In FIG. 27, it is seen that by dividing the full 360° angular extent of a given circular disc (utilizable in place of disc 150 in FIG. 23) into the desired number (n) of indexible steps at 360°/n spacing, and by drawing an ordinate line (e.g., at 120) for each such increment of azimuthal distribution, intercepts (e.g., a-b-c-d-e, for location 120) are obtained for each of five loci, establishing the requisite minor-axis span for each of the involved plural reflecting ellipses at each particular index location. The result for FIG. 27 relationships is myopia-reducing because all outer perimeters (for areas 72-73-74) vary, while inner perimeters remain constant. On the other hand, the result for FIG. 28 relationships is hyperopia-reducing because all inner perimeters (for areas 72′-73′-74″, not otherwise shown) vary, while outer perimeters remain constant, noting intercepts a′-b′-c′-d′-e′-f′ for location 121.

All discussion thus far, for laser projection via indexed reflective areas, has been concerned with essentially spherical curvature correction, treating the myopic or the hyperopic situation, as the case may be. It should, however, also be apparent that similar principles are applicable to astigmatism correction, in which case the pattern of progressively indexed reflecting areas is rectangular, of progressively varying width, symmetrically developed on opposite sides of the central elongate axis of the most narrow rectangular pattern in the progression. The drawing of FIG. 16 may thus be considered illustrative of such a pattern development, wherein the indexible strip 80 is a transparent plate (as of quartz) and the series of rectangles 81 to 81' is reflecting and at equal centerline-to-centerline spacing, with indexing from one centerline (82) to the next, and with the laser-beam axis 12' directed at intersection with the central alignment 86 for each indexed position. It is realized that when strip 80 is supported on guide ring 84 and in an inclined plane as discussed for disc 150 in FIG. 23, the angular orientation of ring 84 (by setting adjustment at 85) will account for a range of width variation in rectangular spots incident at the eye, but the desired cumulative ablation can still be achieved at the eye for any and all selected angular orientations, by entering a suitable angularity correction into the microprocessor, the correction being a simple trigonometric function of orientation angle.

For the above-described reflective uses of the invention, it is to be understood that the individual patterns of reflection are operative upon a portion only of the laser-beam sectional area (on alignment 12'), and that, whether the reflective patterns are mounted to or formed upon a transparent plate (as of quartz) or are otherwise mounted, the portion of any given shot of laser-beam output that is not reflected will be further transmitted on essentially the alignment 12'. This further transmitted energy is not used for the surgery and may be trapped and dissipated by suitable means (not shown).

For the various embodiments thus far described in application to hyperopia-correction, FIG. 10 is illustrative of the fact that penetration into the cornea is deepest at the radially outer limit of the optically corrected area (surface 61), thus leaving a relatively sharp circular edge, of depth proportional to the magnitude of diopter correction achieved. Such a sharp edge presents a problem for epithelial regrowth over the area (61) of surgery, in that epithelial regrowth is optimum for essentially continuous surfaces, i.e., when uninterrupted by sharp edges or by sharp discontinuities. To avoid such a sharp-edge development, the projected laser beam 12 should be of sectional area larger than that over which hyperopia-curvature correction is to be achieved, thus providing for an outer profile-smoothing annulus contiguous to and surrounding the circle of curvature-correction. In FIG. 29, the optically corrected surface 61 is identified as having an outer radius of curvature correction $R_{CC}$, the diameter being shown as $2R_{CC}$; and the outer profile-smoothing annulus is shown to be of radial thickness $\Delta R$, so that the full area of the laser-beam section is of diameter $2(R_{cc}+\Delta R)$. The smoothing action to be described accounts for the gently sloping transitional profile achieved in the annulus $\Delta R$, as suggested in FIG. 29 by dashed lines connecting the curvature-correcting ablated area 61 to the outer corneal area not subjected to ablation.

More particularly, FIG. 30 shows an indexible rotary masking disc 162' of the nature described in connection with FIG. 11 but incorporating the profile-smoothing feature of FIG. 29. Dimensional legends in FIG. 30 show that, at a first index position 163, the masking is such that the projected laser spot is a thin annulus wherein the inner diameter is determined by the outer diameter of the central masking circle 163'; this outer masking diameter is labeled $2R_{cc}$, meaning twice the radius of the corrected-curvature surface 61 (FIG. 29), and in successively indexed positions 164–165, the central masking circle (164'–165') exhibits progressively shrinking diameter, respectively identified $2R_{cc}'$ and $2R_{cc}''$. Also, for these successively indexed positions (164–165), the outer diameter of the projected annular beam 12 exhibits progressive shrinkage, in a first decrement to the diameter $2(R_{cc}+\Delta R')$, and in the next decrement to the diameter $2(R_{cc}+\Delta R')$. These progressive shrinkages continue in successive decrements, with each indexing displacement of disc 162, culminating at a final index position 166, with the smallest central masking circle 166', and with the most-reduced outer diameter $(2R_{cc}+\Delta R/n)$, where n is the number of index positions) equal or substantially equal to the outer diameter $(2R_{cc})$ of the area 61 of hyperopia-corrected curvature.

With a sufficient number n of index positions for disc 162, the cumulative penetration of the cornea develops a smooth profile of the optically corrected surface 61, as well as a smooth profile of the outer transitional annulus.

FIG. 31 provides a schematic description of another means whereby the described smoothing annulus $\Delta R$ may be achieved, without reliance on successively indexed masks. The beam projected from laser 13 is expanded by means 170 so as to project a collimated beam of enlarged section. Fixedly and centrally mounted within the enlarged beam section is a mask device 171 which can be controlled by drive means 172 to exhibit a range of varying outer diameters, illustratively corresponding to the range of diameters for the successive central masks 163' to 166' in FIG. 30. The difference in FIG. 31 is that this outer-diameter progression is smoothly continuous, and mechanical structure at 171 to achieve this result may be adopted from an umbrella, the outer surface of which is preferably reflecting in nature, so that reflected laser-beam energy may be deflected to a surrounding annular absorber 173. A zoom lens 174 focused on the expandable skirt of the umbrella/reflector device 171 is reversibly driven by motor means 175 and a drive circuit 176, so as to progressively change the outer diameter of beam output 12'/12 over the range $2\Delta R$, while the reversible mask-expansion drive 176 is changing the skirt diameter of the umbrella/reflector device 171. A microprocessor 177 is shown connected for coordinating control of laser 13, of the mask drive 177, and of the zoom drive 176.

It will be understood that in discussion of changing diameters and exposures in the various embodiments of this invention, the nature of the change has for the most part been presented as linear, e.g., as in FIGS. 27 and 28. However, for the case of uniform ablative depth penetration (of cornea tissue) per unit time and at a given flux density of laser-beam projection, the relation of diameter change to exposure time is more akin to a square-law function, hence, quasi-parabolic. FIGS. 32 are presented to show that the relation is quasi-parabolic whether the curvature correction is to reduce or eliminate a myopia (FIG. 32) condition, or to reduce or eliminate a hyperopia (FIG. 33) condition.

In each of FIGS. 32 and 33, relative exposure (cumulative flux density of laser-beam impact at the cornea) is displayed as a function of radius, out to $R_{cc}$, the outer radius of curvature correction. In the myopia-correcting case (FIG. 32), maximum exposure is at the center (eye axis), and cumulative exposure decrease to a minimum (effectively zero) at the radius $R_{cc}$. In the hyperopia-correcting case, maximum exposure is at the radius $R_{cc}$, and cumulative exposure decreases to a minimum (effectively zero) at the center; also, it will be noted that in the hyperopia-correcting case, there is a smooth transition from maximum to minimum cumulative exposure in the outer annulus $\Delta R$.

It will be further understood that the linear reduction in cumulative exposure shown in FIG. 33 for the annulus $\Delta R$ will account for minimum slope at all points within the annulus, meaning that for deepest surgical penetration of the cornea (e.g., 100 microns, for a 10-diopter correction over a 5-mm diameter circle of curvature correction), a linear characteristic is best; but for lesser penetrations such as for diopter corrections up to 5 diopters, a non-linear relationship (as suggested by the dashed line spanning $\Delta R$ in FIG. 33) enables provision (within the radial span $\Delta R$) of continuously smooth curvature transition, from the radius $R_{cc}$ of maximum penetration and radially outward to the untreated adjacent original profile of the cornea.

What is claimed is:

1. Sculpture apparatus for curvature-correcting operation upon the anterior surface of the cornea of an eye, comprising laser means producing an output beam in the ultraviolet portion of the electromagnetic spectrum, controllable means for variably limiting the sectional area of said beam at impingement on the cornea, the area variation being over a range which at least includes a maximum curvature-correcting area to be ablated and being symmetrical with respect to a beam-projection axis which coincides with the optical axis of the eye; the intensity of laser-spot projection being limited per unit time to ablate but a fraction of a predetermined maximum depth of ablation into the stroma region of the cornea, and control means connected to said laser means and to said controllable means, for so correlating laser-beam impingement at the cornea with variation of the sectional area of said beam as to effect a diopter change at the cornea.

2. Apparatus for performing ophthalmological surgery by selective ablation of the anterior surface of the cornea of an eye of a patient with penetration into the stroma to achieve a volumetric removal of tissue within the optically functioning area of the cornea, said apparatus comprising laser means producing on an optical axis an output beam in the ultraviolet portion of the electromagnetic spectrum, optical means on said axis including a zoom lens with a zoom drive for variably setting the sectional area of said beam to a spot on the cornea, the area variation of said spot being within a maximum area to be ablated and being symmetrical with respect to a beam-projection axis which coincides with the optical axis of the eye, the intensity of laser-beam projection being limited per unit time to ablate but a fraction of a predetermined maximum ablation into the stroma region of the cornea, and programmable means with coordinating control connections to said laser means and to said zoom drive, whereby the integrated time of laser-beam impingement at the cornea may be so correlated with variable confined-spot area as to effect a diopter-reducing change at the cornea.

3. Sculpture apparatus for curvature-correcting operation upon the anterior surface of the cornea of an eye, comprising laser means producing an output beam in the ultraviolet portion of the electromagnetic spectrum, reflector means for reflecting said beam and for variably limiting the area of said beam at impingement on the cornea, said reflector means including actuating means for varying the reflector area thereof, the range of reflector-area variation at least including a maximum curvature-correcting area to be ablated and being symmetrical with respect to a beam-projection axis which coincides with the optical axis of the eye, the intensity of laser-spot projection being limited per unit time to ablate but a fraction of a predetermined maximum depth of ablation into the stroma region of the cornea, and means including a microprocessor with coordinating control connections to said laser means and to said actuating means, for so correlating laser-beam impingement at the cornea with variation of reflected-spot area as to effect a diopter change at the cornea.

4. Sculpture apparatus according to claim 3, in which said reflector means is operative to provide cornea exposure at a central circular area and at a plurality of similarly shaped but greater areas, said areas being concentric, whereby the diopter change may be myopia-correcting.

5. Sculpture apparatus according to claim 3, in which said reflector means is operative to provide cornea exposure at said maximum area of curvature correction and at a plurality of similarly shaped but lesser areas, said areas being annular and characterized by progressively changing inner radius, whereby the diopter change may be hyperopia-correcting.

6. Sculpture apparatus according to claim 5, in which the range of reflector-area variation is larger than said maximum curvature-correcting area to thereby determine an outer annulus of laser-beam projection surrounding said maximum curvature-correcting area, said actuating means also varying the outer diameter of said outer annulus such that said outer-diameter variation (i) commences at substantially the outer diameter of said curvature-correcting area and (ii) proceeds with outward diameter expansion.

7. Sculpture apparatus according to claim 3, in which said reflector means is operative to provide cornea exposure at a narrow elongate rectangular area centered on the optical axis of the eye and spanning said maximum area, plural said reflector means being further operative to provide cornea exposure at similarly shaped but greater areas, said areas being elongate rectangular and of varying width which is symmetrical about the elongation direction of said narrow area, whereby the diopter change may be astigmatism-correcting.

8. Sculpture apparatus according to claim 7, wherein orientation of the elongate direction of said areas is variable.

9. Sculpture apparatus according to claim 3, in which said reflector means is operative to provide cornea exposure at said maximum area and at a plurality of similarly shaped but lesser areas, said areas being circularly annular, being defined by a constant outer diameter and by an inner diameter which varies to a fixed minimum inner diameter, whereby the diopter change may be myopia-correcting in a sculpted Fresnel annulus defined by said constant outer diameter and by said fixed minimum inner diameter.

10. Sculpture apparatus according to claim 3, in which said reflector means is operative to provide cornea exposure at said maximum area and at a plurality of similarly shaped but lesser areas, said areas being circularly annular, being defined by a constant inner diameter and by a varying outer diameter which is intermediate said inner diameter and the outer diameter of said maximum area, whereby the diopter change may be hyperopia-correcting in a sculpted Fresnel annulus defined by said inner and outer diameters.

11. Sculpture apparatus according to claim 3, in which said reflector means includes a transparent plate having a succession of reflecting elements on a surface thereof, said reflecting elements being of progressively changing area, and microprocessor-controlled means for indexing said reflecting elements into successive alignment with the axis of the laser beam.

12. Sculpture apparatus according to claim 9, in which said reflecting elements are in spaced rectilinear array.

13. Sculpture apparatus according to claim 9, in which said reflecting elements are in spaced array about an axis of index rotation.

14. Sculpture apparatus according to claim 3, in which said reflector means is a variable-aperture diaphragm characterized by a reflective side oriented to reflect the laser beam in a peripherally continuous annular area surrounding the instantaneous diaphragm aperture.

15. Sculpture apparatus according to claim 3, in which laser-beam incidence upon said reflector means is at 45 degrees, and in which the reflector area is always elliptical with a major-axis to minor-axis ratio of $\sqrt{2}:1$, the laser-beam incidence being centered on the ellipse and at 45 degrees to the major-axis thereof.

16. Sculpture apparatus for operation upon the external surface of the cornea of an eye of a patient, comprising laser means producing an output beam in the ultraviolet portion of the electromagnetic spectrum, masking means for variably limiting the area of said beam at impingement on the cornea, said masking means including actuating means for varying the masked area thereof, the range of mask-area variation being within a maximum area to be ablated and being symmetrical with respect to a beam projection axis which coincides with the optical axis of the eye, the intensity of laser-spot projection being limited per unit time to ablate but a fraction of a predetermined maximum ablation into the stroma region of the cornea, said masking means being operative to provide cornea exposure at said maximum area and at a plurality of similarly shaped but lesser areas, said areas being circularly annular, and characterized by varying inner diameter, said areas being further defined by constant outer diameter for an area within which a hyperopia-correcting curvature change is to be effected; said area of curvature change being less than said maximum area thereby defining an annular area of laser-beam projection outside said area of curvature change, said masking means being further operative within said annular area to provide cornea exposure at a succession of circularly annular areas contiguous to the area of curvature change and of varying outer diameter, and means including a microprocessor with coordinating control connections to said laser means and to said actuating means, whereby laser-beam impingement at the cornea may be so correlated with variation of masked-spot area as to effect a hyperopia-correcting diopter change at the cornea, together with a smoothed surrounding annulus of transition to adjacent unexposed corneal tissue.

17. Sculpture apparatus according to claim 1, in which said control means is further connected to said laser means and to said controllable means, for so correlating laser-beam impingement at the cornea with beam-section veriation in an outer annular area which is contiguous to the curvature-correcting area of diopter change as to effect a graduated radially outward transition (a) from the depth of stroma ablation at the perimeter of diopter change and (b) to substantially zero depth at the outer limit of said annular area.

18. Apparatus for performing ophthalmological surgery by selective ablation of the anterior surface of the cornea of an eye of a patient with penetration into the stroma to achieve a volumetric removal of tissue within the optically functioning area of the cornea, said apparatus comprising laser means producing on an optical axis an output beam in the ultraviolet portion of the electromagnetic spectrum, optical means on said axis including a zoom lens with a zoom drive for variably setting the sectional area of said beam to a spot on the cornea, the area variation of said spot being within a maximum area to be ablated and being symmetrical with respect to a beam-projection axis which coincides with the optical axis of the eye, the intensity of laser-beam projection being limited per unit time to ablate but a fraction of a predetermined maximum ablation into the stroma region of the cornea, and means including a microprocessor with coordinating control connections to said laser means and to said zoom drive, whereby the integrated time of laser-beam impingement at the cornea may be so correlated with variable confined-spot area as to effect a diopter-reducing change at the cornea.

19. Apparatus according to claim 18 or claim 2, in which said zoom lens is of a variety to convert said output beam into a confined circular section of area which varies in accordance with variation in the setting of said zoom drive, whereby the diopter-reducing change may be myopia-correcting.

20. Apparatus according to claim 18 or claim 2, in which said zoom lens is of a variety to convert said output beam into a confined straight line extending diametrically through the optical axis, said line being of width which varies in accordance with variation in the setting of said zoom drive, whereby the diopter-reducing change may be corrective of astigmatism.

21. Apparatus according to claim 18 or claim 2, in which said zoom lens is of a variety to convert said output beam into a confined straight line extending diametrically through the optical axis, said line being of width which varies in accordance with variation in the setting of said zoom drive, whereby the diopter-reducing change may be corrective of astigmatism, and in which said zoom lens has an optical axis and is mounted for selective bodily rotation about its optical axis, whereby the angular orientation of said straight line may be set to accord with that of required astigmatism correction.

22. Apparatus for performing ophthalmological surgery by selective ablation of the anterior surface of the cornea of an eye of a patient with penetration into the stroma to achieve a volumetric removal of tissue within the optically functioning area of the cornea, said apparatus comprising laser means producing on an optical axis an output beam in the ultraviolet portion of the electromagnetic spectrum, masking means for variably limiting the sectional area of said beam at impingement on the cornea, said masking means including actuating means for varying the sectional area masked by said masking means, the mask-area variation being over a range of areas within a maximum area to be ablated and being symmetrical with respect to a beam projection axis which coincides with the optical axis of the eye, the intensity of laser-beam projection being limited per unit time to ablate but a fraction of a predetermined maximum ablation into the stroma of the cornea, and means including a microprocessor with coordinating control connections to said laser means and to said actuating means, whereby laser-beam impingement at the cornea may be so correlated with variation of sectional area as to effect a diopter change at the cornea.

23. Apparatus for performing ophthalmological surgery by selective ablation of the anterior surface of the cornea of an eye of a patient with penetration into the stroma to achieve a volumetric removal of tissue within the optically functioning area of the cornea, said apparatus comprising laser means producing on an optical axis an output beam in the ultraviolet portion of the electromagnetic spectrum, masking means for variably limiting the sectional area of said beam at impingement on the cornea, said masking means including actuating means for varying the sectional area marked by said masking means, the mask-area variation being over a range of areas within a maximum area to be ablated and being symmetrical with respect to a beam projection axis which coincides with the optical axis of the eye, the intensity of laser-beam projection being limited per unit time to ablate but a fraction of a predetermined maximum ablation into the stroma of the cornea, and programmable means with coordinating control connections to said laser means and to said actuating means, whereby laser-beam impingement at the cornea may be so correlated with variation of sectional areas as to effect a diopter change at the cornea.

24. Apparatus according to claim 22 or claim 23, in which said masking means is operative to provide cornea exposure at said maximum area and at a plurality of similarly shaped but lesser areas, said areas being elongate rectangular and of varying width, whereby the diopter change may be astigmatism-correcting.

25. Apparatus according to claim 22 or claim 23, in which said masking means is operative to provide cornea exposure at said maximum area and at a plurality of similarly shaped but lesser areas, said areas being elongate rectangular and of varying width, whereby the diopter change may be astigmatism-correcting, and wherein orientation of the elongate direction of said areas is variable.

26. Apparatus according to claim 22 or claim 23, in which said masking means is operative to provide cornea exposure at said maximum area and at a plurality of similarly shaped but lesser areas, said areas being circularly annular, being defined by a constant outer diameter and by a varying inner diameter, whereby the diopter change may be hyperopia-correcting.

27. Apparatus according to claim 22 or claim 23, in which said masking means is operative to provide cornea exposure at said maximum area and at a plurality of similarly shaped but lesser areas, said areas being circularly annular, being defined by a constant inner diameter and by a varying outer diameter which is intermediate said inner diameter and the outer diameter of said maximum area, whereby the diopter change may be myopia-correcting in a sculpted Fresnel annulus defined by said inner and outer diameters.

28. Apparatus according to claim 2 or claim 23, in which said masking means is operative to provide cornea exposure at said maximum area and at a plurality of similarly shaped but lesser areas, said areas being circularly annular, being defined by a constant outer diameter and by an inner diameter which varies to a fixed minimum inner diameter, whereby the diopter change may be hyperopia-correcting in a sculpted Fresnel annulus defined by said constant outer diameter and by said fixed minimum inner diameter.

29. Apparatus according to claim 22 or claim 23, in which said masking means includes an opaque plate having a succession of windows which are (a) transparent to laser-beam transmission therethrough and (b) of progressively changing area, and in which said microprocessor-controlled means is connected to index said windows into successive alignment with the axis of the laser beam.

30. Apparatus according to claim 22 or claim 23, in which said masking means includes an opaque plate having a succession of windows which are (a) transparent to laser-beam transmission therethrough and (b) of progressively changing area, and in which said microprocessor-controlled means is connected to index said windows into successive alignment with the axis of the laser beam, and in which said windows are in spaced rectilineal array.

31. Apparatus according to claim 22 or claim 23, in which said masking means includes an opaque plate having a succession of windows which are (a) transparent to laser-beam transmission therethrough and (b) of progressively changing area, and in which said microprocessor-controlled means is connected to index said windows into successive alignment with the axis of the laser beam, and in which said windows are in spaced circular array.

32. Apparatus according to claim 22 or claim 23, in which said masking means is operative to provide cornea exposure at said maximum area and at a plurality of similarly shaped but lesser areas, said areas being circular, whereby the diopter change may be myopia-correcting.

33. Apparatus according to claim 22 or claim 23, in which said masking means includes an opaque plate having a succession of windows which are (a) transparent to laser-beam transmission therethrough and (b) of progressively changing area, and in which said programmable means is connected to index said windows into successive alignment with the axis of the laser beam.

34. Apparatus according to claim 22 or claim 23, in which said masking means includes an opaque plate having a succession of windows which are (a) transparent to laser-beam transmission therethrough and (b) of progressively changing area, and in which said programmable means is connected to index said windows into successive alignment with the axis of the laser beam, and in which said windows are in spaced rectilineal array.

35. Apparatus according to claim 22 or claim 23, in which said masking means includes an opaque plate having a succession of windows which are (a) transparent to laser-beam transmission therethrough and (b) of progressively changing area, and in which said programmable means is connected to index said windows into successive alignment with the axis of the laser beam, and in which said windows are in spaced circular array.

36. Apparatus for performing ophthalmological surgery by selective ablation of the anterior surface of the cornea of an eye of a patient with penetration into the stroma to achieve a volumetric removal of tissue within the optically functioning area of the cornea, said apparatus comprising laser means producing on an optical axis an output beam in the ultraviolet portion of the electromagnetic spectrum, optical means including reflector means for reflecting said beam on said axis and for variably limiting the sectional area of said beam at impingement on the cornea, said reflector means including actuating means for varying the reflecting area thereof, the reflecting-area variation being over a range producing reflected-beam section areas within a maximum area to be ablated and being symmetrical with respect to a beam-projection axis adapted for alignment with the optical axis of the eye, the intensity of the projected beam being limited per unit time to ablate but a fraction of a predetermined maximum ablation into the stroma of the cornea, and means including a microprocessor with coordinating control connections to said laser means and to said actuating means, whereby laser-beam impingement at the cornea may be so correlated with variation of reflected-beam section areas as to effect a diopter change at the cornea.

37. Apparatus according to claim 36, in which laser-beam incidence upon said reflector means is at 45 degrees, and in which the reflecting area is always elliptical with a major-axis to minor-axis ratio of $\sqrt{2:1}$, the laser-beam incidence being centered on the ellipse and at 45 degrees to the major-axis thereof.

38. Apparatus for performing ophthalmological surgery by selective ablation of the anterior surface of the cornea of an eye of a patient with penetration into the stroma to achieve a volumetric removal of tissue within the optically functioning area of the cornea, said apparatus comprising laser means producing on an optical axis an output beam in the ultraviolet portion of the electromagnetic spectrum, optical means including reflector means for reflecting said beam on said axis and for variably limiting the sectional area of said beam at impingement on the cornea, said reflector means including actuating means for varying the reflecting area thereof, the reflecting-area variation being over a range producing reflected-beam section areas within a maximum area to be ablated and being symmetrical with respect to a beam-projection axis adapted for alignment with the optical axis of the eye, the intensity of the projected beam being limited per unit time to ablate but a fraction of a predetermined maximum ablation into the stroma of the cornea, and programmable means with coordinating control connections to said laser means and to said actuating means, whereby laser-beam impingement at the cornea may be so correlated with variation of reflected-beam section area as to effect a diopter change at the cornea.

39. Apparatus according to claim 36 or claim 38, in which said reflector means is operative to provide cornea exposure at a narrow elongate rectangular area centered on the optical axis of the projected beam and spanning said maximum area, said reflector means being further operative to provide cornea exposure at a plurality of similarly shaped but greater areas, said areas being elongate rectangular and of varying width which is symmetrical about the elongate direction of said narrow area, whereby the diopter change may be astigmatism-correcting.

40. Apparatus according to claim 36 or claim 38, in which said reflector means is operative to provide cornea exposure at a narrow elongate rectangular area centered on the optical axis of the projected beam and spanning said maximum area, said reflector means being further operative to provide cornea exposure at a plurality of similarly shaped but greater areas, said areas being elongate rectangular and of varying width which is symmetrical about the elongate direction of said narrow area, whereby the diopter change may be astigmatism-correcting, and wherein orientation of the elongate direction of said areas is variable.

41. Apparatus according to claim 36 or claim 38, in which said reflector means is operative to provide cornea exposure at said maximum area and at a plurality of similarly shaped but lesser areas, said areas being circularly annular, being defined by a constant outer diameter and by an inner diameter which varies to a fixed minimum inner diameter, whereby the diopter change may be hyperopia-correcting in a sculpted Fresnel annulus defined by said constant outer diameter and by said fixed minimum inner diameter.

42. Apparatus according to claim 36 or claim 38, in which said reflector means is operative to provide cornea exposure at said maximum area and at a plurality of similarly shaped but lesser areas, said areas being circularly annular, being defined by a constant inner diameter and by a varying outer diameter which is intermediate said inner diameter and the outer diameter of said maximum area, whereby the diopter change may be myopia-correcting in a sculpted Fresnel annulus defined by said inner and outer diameters.

43. Apparatus according to claim 36 or claim 38, in which said reflector means includes a transparent plate having a succession of reflecting elements on a surface thereof, said reflecting elements being of progressively changing area, and in which said microprocessor-controlled means is connected to index said reflecting elements into successive alignment with the axis of the laser beam.

44. Apparatus according to claim 36 or claim 38, in which said reflector means includes a transparent plate having a succession of reflecting elements on a surface thereof, said reflecting elements being of progressively changing area, and in which said microprocessor-controlled means is connected to index said reflecting elements into successive alignment with the axis of the laser beam, and in which said reflecting elements are in spaced rectilineal array.

45. Apparatus according to claim 36 or claim 38, in which said reflector means includes a transparent plate having a succession of reflecting elements on a surface thereof, said reflecting elements being of progressively changing area, and in which said microprocessor-controlled means is connected to index said reflecting elements into successive alignment with the axis of the laser beam, and in which said reflecting elements are in spaced array about an axis of index rotation.

46. Apparatus according to claim 36 or claim 38, in which said reflector means is a variable-aperture diaphragm characterized by a reflective side oriented to reflect the laser beam in a peripherally continuous annular area surrounding the diaphragm aperture.

47. Apparatus according to claim 36 or claim 38, in which said reflector means is operative to provide cornea exposure at a central circular area and at a plurality of similarly shaped but greater areas, said areas being concentric, whereby the diopter change may be myopia-correcting.

48. Apparatus according to claim 36 or claim 38, in which said reflector means is operative to provide cornea exposure at said maximum area and at a plurality of similarly shaped but lesser areas, said areas being annular and characterized by varying inner radius within said maximum area, whereby the diopter change may be hyperopia-correcting.

* * * * *

UNITED STATES PATENT AND TRADEMARK OFFICE
CERTIFICATE OF CORRECTION

PATENT NO. : 4,729,372
DATED : March 8, 1988
INVENTOR(S) : Francis A. L'Esperance, Jr.

It is certified that error appears in the above-identified patent and that said Letters Patent is hereby corrected as shown below:

On Abstract page, at [60] Related U.S. Application Data, should read:

-- Continuation-in-part of copending application Serial No. 778,801, filed Sept. 23, 1985 (now abandoned) and said copending application is a continuation-in-part of application Serial No. 742,225, filed June 6, 1985 (now abandoned). Said application Ser. No. 742,225 is a continuation-in-part of my original application Ser. No. 552,983, filed Nov. 17, 1983 (now abandoned), and applications Ser. Nos. 807,226, filed Dec. 10, 1985 (now abandoned) and 807,239, filed Dec. 10, 1985 (now abandoned) are apparatus divisionals of said applications Ser. Nos. 742,225 and 778,801, respectively. --

Col. 1  Line 8  should read -- (now abandoned) --
        Line 13 should read -- abandoned) --

Col. 11 Lines 3, 36, and 59, and at Claim 15, line 4 and Claim 37, line 4, the expression should read -- $\sqrt{2}:1$, as the application text reads.

Claim 17 Line 5  "veriation" should be -- variation --.

Signed and Sealed this

Twenty-sixth Day of July, 1988

Attest:

DONALD J. QUIGG

Attesting Officer

Commissioner of Patents and Trademarks